US007085603B1

(12) United States Patent
Florio et al.

(10) Patent No.: US 7,085,603 B1
(45) Date of Patent: *Aug. 1, 2006

(54) SYSTEM AND METHOD FOR AUTOMATICALLY VERIFYING CAPTURE DURING MULTI-CHAMBER STIMULATION

(75) Inventors: Joseph J. Florio, La Canada, CA (US); Euljoon Park, Valencia, CA (US); Kerry Bradley, Glendale, CA (US); Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 501 days.

This patent is subject to a terminal disclaimer.

(21) Appl. No.: 10/353,104

(22) Filed: Jan. 27, 2003

Related U.S. Application Data

(63) Continuation of application No. 09/844,189, filed on Apr. 26, 2001, now Pat. No. 6,512,953.

(60) Provisional application No. 60/203,688, filed on May 11, 2000.

(51) Int. Cl.
*A61N 1/365* (2006.01)
(52) U.S. Cl. ...................................................... 607/28
(58) Field of Classification Search ............. 607/9–28
See application file for complete search history.

(56) References Cited

U.S. PATENT DOCUMENTS 6,512,953 B1 * 1/2003 Florio et al. .................. 607/28

* cited by examiner

*Primary Examiner*—Scott M. Getzow

(57) ABSTRACT

A system and corresponding method are provided to reliably detect capture during multi-chamber stimulation, and to further monitor the progression of congestive heart failure. The system provides a method by which intracardiac electrogram (IEGM) characteristics representing single-chamber capture and bi-ventricular capture are stored in memory and displayed. The annotation of the displayed waveforms is such that events associated with loss of capture, single-chamber capture, and bi-ventricular capture are clearly marked for ready interpretation by the physician. In a first situation, a stimulation pulse is followed by a time delay window and a subsequent depolarization complex that represents intrinsic responses of the chambers that have not been captured. In a second situation, a stimulation pulse is followed almost immediately by an evoked response that represents capture of one chamber, and a subsequent depolarization complex that represents an intrinsic response of one chamber that has not been captured. In a third situation, a stimulation pulse is almost immediately followed by an evoked response that represents simultaneous capture of two chambers.

16 Claims, 9 Drawing Sheets

FIG. 3C
PRIOR ART
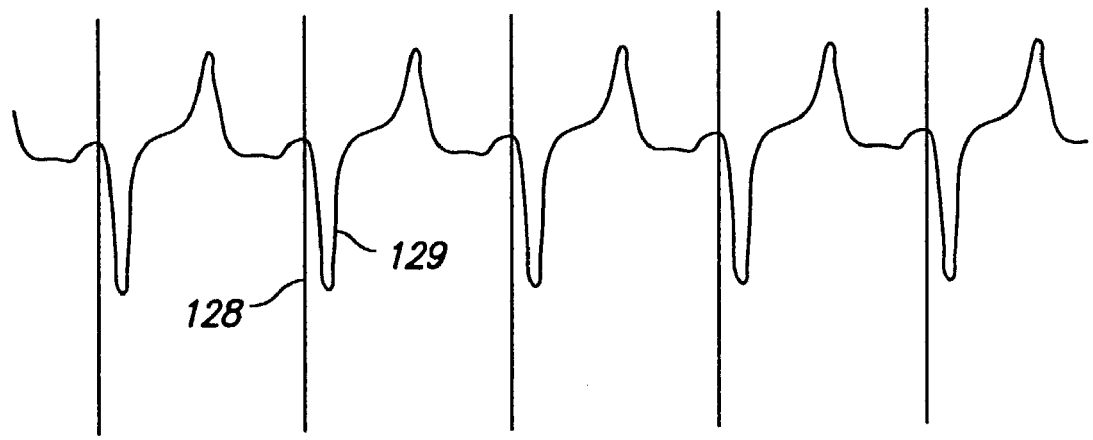
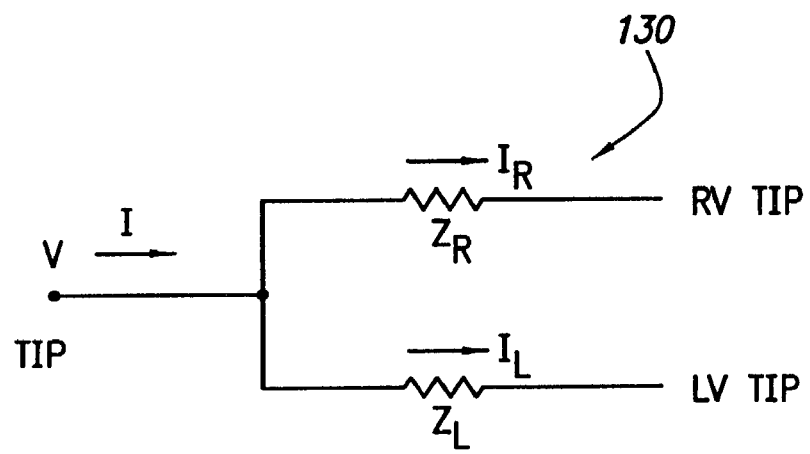
FIG. 4A

SYSTEM AND METHOD FOR AUTOMATICALLY VERIFYING CAPTURE DURING MULTI-CHAMBER STIMULATION

CROSS-REFERENCE TO RELATED APPLICATIONS

This application is a continuation of U.S. patent application Ser. No. 09/844,189, filed Apr. 26, 2001, now U.S. Pat. No. 6,512,953, and entitled "System and Method for Automatically Verifying Capture During Multi-Chamber Stimulation", which in turn claims the priority of provisional U.S. Application Ser. No. 60/203,688, filed May 11, 2000, which is incorporated herein by reference in its entirety.

FIELD OF THE INVENTION

This invention relates generally to a programmable cardiac stimulating apparatus for the purpose of automatically verifying capture during multi-chamber stimulation. More specifically, the present invention is directed to an implantable stimulation device and associated method for automatically verifying simultaneous capture during bi-ventricular or bi-atrial stimulation, also referred to herein as bi-chamber stimulation or two corresponding chamber stimulation.

BACKGROUND OF THE INVENTION

Congestive heart failure (CHF) is a debilitating, end-stage disease in which abnormal function of the heart leads to inadequate blood flow to fulfill the needs of the body's tissues. Typically, the heart loses propulsive power because the cardiac muscle loses capacity to stretch and contract. Often, the ventricles do not adequately fill with blood between heartbeats and the valves regulating blood flow may become leaky, allowing regurgitation or back flow of blood. The impairment of arterial circulation deprives vital organs of oxygen and nutrients. Fatigue, weakness, and inability to carry out daily tasks may result.

Not all CHF patients suffer debilitating symptoms immediately. Some may live actively for years. Yet, with few exceptions, the disease is relentlessly progressive.

As CHF progresses, it tends to become increasingly difficult to manage. Even the compensatory responses it triggers in the body may themselves eventually complicate the clinical prognosis. For example, when the heart attempts to compensate for reduced cardiac output, it adds muscle causing the ventricles to grow in volume in an attempt to pump more blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in providing cardiac output.

CHF has been classified by the New York Heart Association (NYHA). Their classification of CHF corresponds to four stages of progressively worsening symptoms and exercise capacity from Class I to Class IV. Class I corresponds to no limitation wherein ordinary physical activity does not cause undue fatigue, shortness of breath, or palpitation. Class II corresponds to slight limitation of physical activity wherein such patients are comfortable at rest, but where ordinary physical activity results in fatigue, shortness of breath, palpitations, or angina. Class III corresponds to a marked limitation of physical activity wherein, although patients are comfortable at rest, less than ordinary activity will lead to symptoms. Class IV corresponds to inability to carry on any physical activity without discomfort, wherein symptoms of CHF are present even at rest and where with any physical activity, increased discomfort is experienced.

Current standard treatment for heart failure is typically centered around medical treatment using ACE inhibitors, diuretics, and digitalis. It has also been demonstrated that aerobic exercise may improve exercise tolerance, improve quality of life, and decrease symptoms. Only an option in approximately 1 out of 200 cases, heart transplantation is also available. Other cardiac surgery is also indicated for only a small percentage of patients with particular etiologies. Although advances in pharmacological therapy have significantly improved the survival rate and quality of life of patients, patients in NYHA Classes III or IV, who are still refractory to drug therapy, have a poor prognosis and limited exercise tolerance. Cardiac pacing has been proposed as a new primary treatment for patients with drug-refractory CHF.

By tracking the progression or regression of CHF more closely, treatments could be administered more effectively. Commonly, patients adapt their lifestyle and activities to their physical condition. The activity level of the patients with NYHA Class III or IV would be much lower than that of the patients with NYHA Class I or II. The change in lifestyle or activity level, due to the patient's heart condition, will be reflected by activity and respiration physiological parameters.

Besides various assessments of the cardiac function itself, assessment of activity and respiration are typically performed. This includes maximal exercise testing in which the heart rate and maximum ventilation are measured during peak exertion. However, peak exercise performance has been found to not always correlate well with improvements in a patient's clinical conditions. Therefore, sub-maximal exercise testing can also be performed, such as a six-minute walk test. While improvements in sub-maximal exercise may suggest an improvement in clinical condition, sub-maximal exercise performance can be variable in that it is dependent on how the patient happens to be feeling on the particular day of the test.

As CHF progresses, the dilation of the heart chambers alters the normal conduction time of the electrical signals through the heart. These electrical signals coordinate the depolarization and subsequent contraction of the heart chambers. Bi-ventricular pacing is expected to improve the coordination of heart chambers by reducing the right ventricle (RV) contraction time and the left ventricle (LV) contraction time, and by increasing the diastolic filling time.

One challenge in bi-ventricular pacing is the ability to detect and verify capture of both ventricles. Since the benefit of bi-ventricular pacing is derived only when capture of both chambers is achieved, proper determination of pacing threshold for each ventricle, or both combined, is imperative to a successful therapy delivery. During device implantation, physicians often rely on ECG recordings to observe when a stimulating pulse is of sufficient energy to cause heart contraction, a condition known as "capture." The lowest stimulation pulse energy sufficient to capture the heart is referred to as "capture threshold."

FIGS. 3A, 3B and 3C depict three surface ECG recordings for three exemplary capture situations during bi-ventricular pacing. FIG. 3A represents a surface ECG recording during sub-threshold bi-ventricular pacing, and illustrates the failure to capture both the left and right ventricles. FIG. 3A shows a stimulation pulse 120 followed by a natural depolarization complex 124, with a time delay 125 therebetween. In FIG. 3A neither ventricle is captured, and the intrinsic responses of both ventricles are represented by the depolarization complex 124.

FIG. 3B represents a surface ECG during bi-ventricular pacing in which the capture of only one ventricle (i.e., the right ventricle) but not the other ventricle (i.e., the left ventricle) is achieved. A ventricular stimulation pulse 126 is followed immediately by a depolarization complex 127 which is a complex representing both the evoked response of the captured ventricle and the intrinsic response of the other ventricle that has not been captured. The evoked response to the stimulation pulse 126 in one ventricle is conducted naturally to the other ventricle causing a second depolarization. The conducted response of the other ventricle slightly lags the evoked response in the captured ventricle in accordance with the inter-ventricular conduction delay. This slight delay, however, is not distinguishable on the surface ECG. Since two distinct events are not easily discernible, recognition of only single-chamber capture versus bi-ventricular capture from the ECG recording alone is quite difficult.

FIG. 3C represents a surface ECG during bi-ventricular pacing when successful capture of both ventricles is achieved. A stimulation pulse 128 is followed immediately by a depolarization complex 129 representing the evoked response of both ventricles. This ECG recording appears generally similar to the ECG recording of FIG. 3B in which only one chamber was captured. As a result, differentiation between single-chamber capture (FIG. 3B) and bi-ventricular capture (FIG. 3C) is therefore difficult and impractical from a surface ECG recording. An inappropriately selected ventricular stimulation pulse energy could be harmful to the patient if only one ventricle is captured because poor synchronization between chambers could lead to arrhythmias.

Implantable cardiac stimulating devices contain sensing circuitry for monitoring the patient's internal heartbeat signals. These internal heartbeat signals are commonly referred to as the intracardiac electrogram ("IEGM"). Cardiac stimulating devices monitor the IEGM to determine precisely when stimulation pulses should be applied. For example, some implantable cardiac stimulating devices such as demand pacemakers apply electrical stimulation pulses to the heart only in the event that the patient's heart fails to beat properly on its own. By applying stimulation pulses only when needed, it is possible to avoid competition between the pulses applied by the device and the patient's intrinsic cardiac rhythm.

Cardiac stimulating devices process the IEGM to determine what type of electrical pulses should be applied to the patient's heart. Other cardiac devices, known as cardiac monitoring devices, are used solely to monitor the patient's cardiac condition. Cardiac monitoring devices are similar to cardiac stimulating devices, but do not contain pulse generating circuitry. Both cardiac stimulating devices and cardiac monitoring devices process the IEGM to identify various cardiac events. For example, an implantable cardiac device with atrial sensing circuitry can detect P-waves that accompany atrial contractions. Ventricular sensing circuitry can be used to detect R-waves that accompany the contraction of the patient's ventricles.

Cardiac stimulating devices additionally process the IEGM in order to verify that a stimulating pulse is of sufficient energy to capture. The lowest capture threshold is sought in order to conserve battery energy while maintaining effective therapy delivery. Numerous schemes for processing the IEGM to determine threshold and to detecting capture are described for example in U.S. Pat. No. 5,766,229 to Bornzin, U.S. Pat. No. 5,778,881 to Sun et al., and U.S. Pat. No. 5,324,310 to Greeninger et al.

However, conventional capture detection methods generally address the need to determine threshold and to verify capture in single-chamber pacing, specifically the right ventricle, or dual chamber pacing, specifically the right atrium and right or left ventricle. Therefore, a need still exists to detect threshold and capture during multi-chamber pacing configurations, particularly during bi-ventricular pacing in CHF patients.

In dual-chamber atrial-ventricular pacing, an atrial pulse generator and atrial sense amplifier are connected to the atrial lead, and a ventricular pulse generator and ventricular sense amplifier are connected to a ventricular lead. This allows separate sensing of atrial events and ventricular events to allow for distinct monitoring of atrial and ventricular threshold and capture detection. In a bi-ventricular pacing system, however, the ventricular channel can be bifurcated and connected to both the right ventricle lead and the left ventricle lead, with typically only one ventricular sense amplifier and one ventricular pulse generator, thus preventing the ventricles from being monitored or paced separately. Therefore, a method is needed that allows monitoring of the right ventricle and the left ventricle threshold and capture detection using existing hardware or circuitry.

Furthermore, a method of tracking the progression or regression of CHF during delivery of chronic pacing therapies would allow treatment to be administered more effectively.

A number of attempts have been made previously to provide for chronic monitoring of physiological parameters associated with CHF using implantable cardiac devices, such as pacemakers, in conjunction with physiological sensors. Reference is made to U.S. Pat. No. 5,518,001 to Snell et. al.; U.S. Pat. No. 5,944,745; U.S. Pat. No. 5,974,340 to Kadhiresan; U.S. Pat. No. 5,935,081 to Kadhiresan; U.S. Pat. No. 6,021,351 to Kadhiresan et al.

However, as CHF progresses, the dilation of the ventricles increases, causing inter-ventricular conduction time to increase. Therefore, it would be desirable to have a method that automatically and accurately monitors inter-ventricular conduction time during bi-ventricular pacing as a means for monitoring CHF progression.

SUMMARY

The present invention addresses these needs by providing an implantable stimulation device that reliably detects bi-chamber capture during multi-chamber pacing, measures the interchamber conduction delay to monitor the progression of CHF and to optimize therapy delivery. These goals are achieved without additional hardware or circuitry.

While the events of single-chamber capture verses both chamber capture are difficult to distinguish on a surface ECG, they are clearly visible on an IEGM.

The present invention is capable of sensing a composite cardiac signal on a single sense channel that has, inherent in it, characteristics that permit the detection of non-capture, single-chamber capture, and bi-chamber capture. While the illustrated embodiments are directed towards a bi-ventricular stimulation device, the present invention can be equally applied in a bi-atrial mode of stimulation.

Thus, one aspect of the present invention is to provide a method by which an IEGM characteristic representing non-capture, single-chamber capture and bi-ventricular capture are stored in memory.

In one embodiment, the IEGM characteristics for non-capture, single-chamber capture and bi-ventricular capture are compared to newly acquired IEGM waveforms during normal operation of the stimulation device, to determine whether the newly acquired IEGM represents failed capture, single-chamber capture, or bi-ventricular capture.

In an alternative embodiment, sampled IEGM waveforms during both single-chamber capture and bi-ventricular capture are processed by a morphology detector that measures and stores defining characteristics of the single-chamber capture and bi-ventricular capture. For example, peak detection, slope detection, waveform integration, and timing interval estimation can be performed with results stored in memory. Then, during normal operation of the stimulation device, a newly sampled IEGM waveform can be processed in the same way to allow comparison of its waveform characteristics to single-chamber capture or bi-ventricular capture characteristics. In this way, reliable and automatic detection of capture during bi-ventricular pacing is achieved.

A further aspect of the present invention is to provide a temporary high ventricular stimulation pulse energy if correlation between a newly sampled IEGM and the bi-ventricular template or the bi-ventricular waveform properties is poor. This high stimulation energy allows bi-ventricular capture to be regained. The device may then update the single-chamber capture and the bi-ventricular capture IEGM characteristics for future capture detection.

In one embodiment, the method of detecting bi-chamber capture may exist in an external cardiac stimulation device, such as a temporary pacing device, a pacing system analyzer or a programmer capable of performing capture tests. In this embodiment, an automatic display feature allows for the display of the acquired IEGM waveforms. A further feature is the annotation of the displayed waveforms such that events associated with loss of capture, single-chamber capture, and bi-ventricular capture are clearly marked for the physician to interpret.

Yet a further aspect of the present invention is to provide a method by which progression of CHF can be monitored. During the acquisition phase of the single-chamber template or waveform characteristic, the time interval between the evoked response of the captured ventricle and the conducted response in the non-captured ventricle can be measured as an estimation of the inter-ventricular conduction time. This measurement can be stored in memory to be available during patient follow-up such that worsening of CHF can be detected. Furthermore, a worsening or improving of the inter-ventricular conduction time could be used as feedback within the stimulation device to adjust stimulation parameters in a way that optimizes the stimulation therapy.

BRIEF DESCRIPTION OF THE DRAWINGS

The above and further features, advantages and benefits of the present invention will be apparent upon consideration of the present description taken in conjunction with the accompanying drawings, in which:

FIG. 3C represents a conventional surface ECG during bi-ventricular pacing in which successful capture of both ventricles is achieved;

FIG. 4A is a circuit diagram representing an equivalent circuit of the stimulation device of FIG. 1 for bi-ventricular pacing through a bifurcated connector of the stimulation device of FIG. 1;

DETAILED DESCRIPTION OF PREFERRED EMBODIMENTS

The following description is of a best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout. While the following description is directed towards a bi-ventricular method of stimulating the heart, the present invention includes applying the method in both of the atria to perform bi-atrial stimulation.

Figure 1:
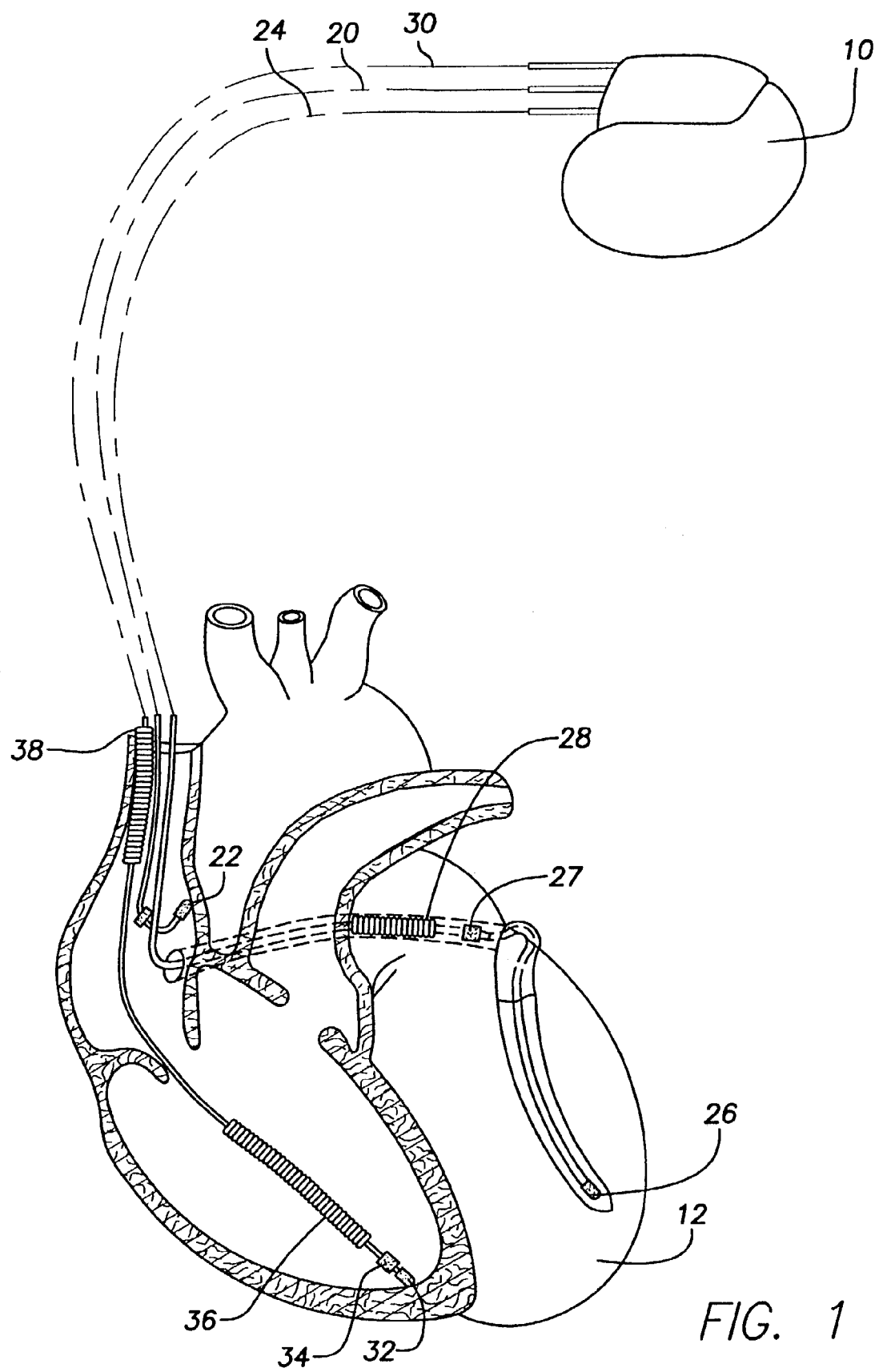
FIG. 1 is a simplified, partly cutaway view illustrating an implantable stimulation device in electrical communication with at least three leads implanted into a patient's heart for delivering multi-chamber stimulation and shock therapy.

FIG. 1 illustrates a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left-chamber stimulation therapy, the stimulation device 10 is coupled to a "coronary sinus" lead 24 designed for placement in the "coronary sinus region" via the coronary sinus os so as to place a distal electrode adjacent to the left ventricle and additional electrode(s) adjacent to the left atrium. As used herein, the phrase "coronary sinus region"

refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver: left ventricular stimulation therapy using at least a left ventricular tip electrode 26, left atrial stimulation therapy using at least a left atrial ring electrode 27, and shocking therapy using at least a left atrial coil electrode 28. For a more detailed description of a coronary sinus lead, reference is made to U.S. patent application Ser. No. 09/457,277, filed Dec. 8, 1999, titled "A Self-Anchoring, Steerable Coronary Sinus Lead" (Pianca et. al), which is a continuation-in-part of application Ser. No. 09/196,898, filed Nov. 20, 1998 (now abandoned), which is incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
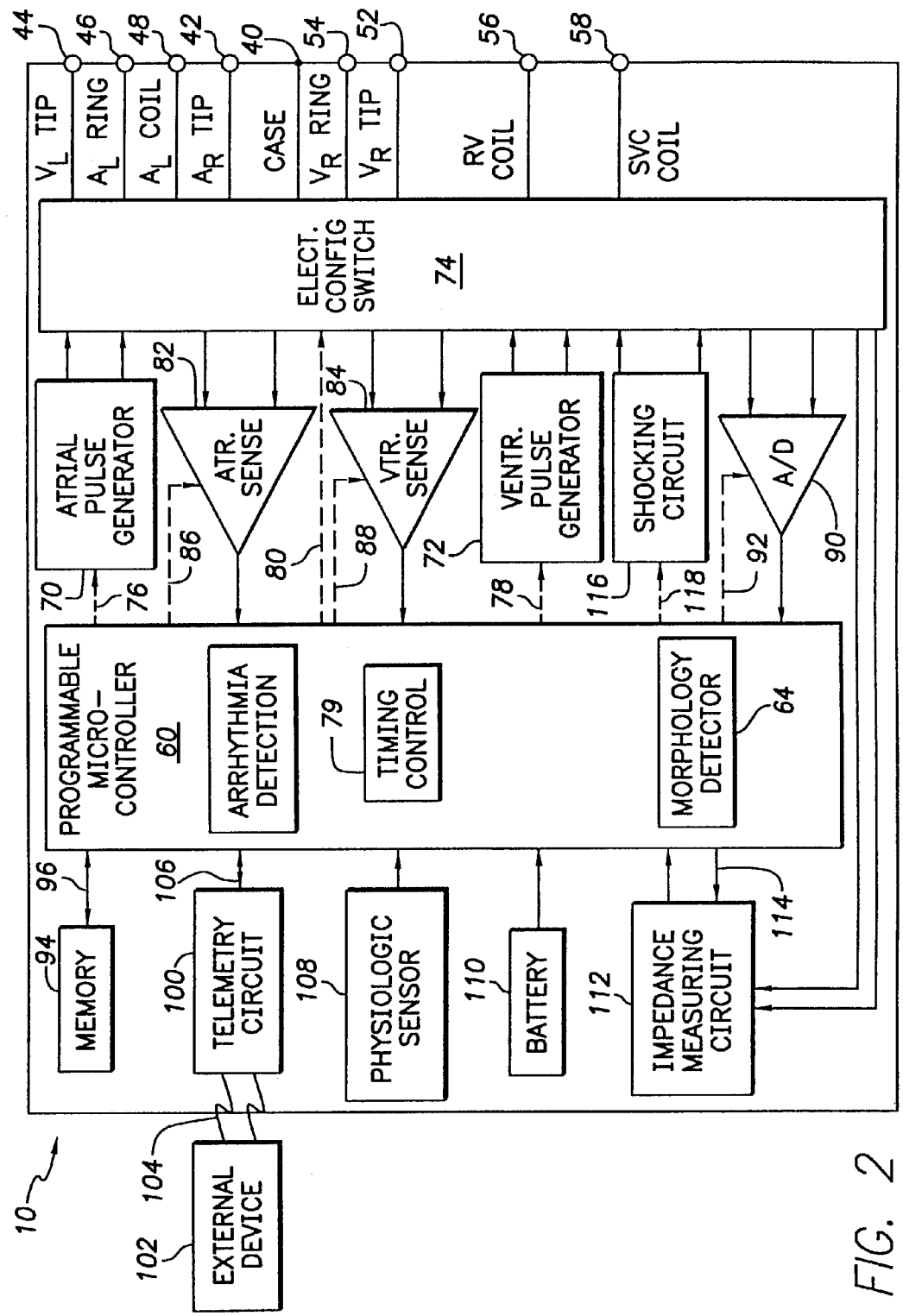
FIG. 2 is a functional block diagram of the multi-chamber implantable stimulation device of FIG. 1, illustrating the basic elements that provide cardioversion, defibrillation and/or pacing stimulation in four chambers of the heart.

FIG. 2 illustrates a simplified block diagram of the multi-chamber implantable stimulation device 10, which is capable of treating both fast and slow arrhythmias with stimulation therapy, including cardioversion, defibrillation, and stimulation stimulation. While a particular multi-chamber device is shown, this is for illustration purposes only, and one of skill in the art could readily duplicate, eliminate, or disable the appropriate circuitry in any desired combination to provide a device capable of treating the appropriate chamber(s) with cardioversion, defibrillation and/or pacing stimulation.

The stimulation device 10 includes a housing 40 which is often referred to as "can", "case" or "case electrode", and which may be programmably selected to act as the return electrode for all "unipolar" modes. The housing 40 may further be used as a return electrode alone or in combination with one or more of the coil electrodes 28, 36, or 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and stimulation, the connector includes at least a right atrial tip terminal 42 adapted for connection to the atrial ($A_R$) tip electrode 22.

To achieve left chamber sensing, pacing and/or shocking, the connector includes at least a left ventricular ($V_L$) tip terminal 44, a left atrial ($A_L$) ring terminal 46, and a left atrial ($A_L$) shocking terminal (coil) 48, which are adapted for connection to the left ventricular tip electrode 26, the left atrial tip electrode 27, and the left atrial coil electrode 28, respectively.

To support right chamber sensing, pacing and/or shocking, the connector further includes a right ventricular ($V_R$) tip terminal 52, a right ventricular ($V_R$) ring terminal 54, a right ventricular (RV) shocking terminal (coil) 56, and an SVC shocking terminal (coil) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. As is well known in the art, the microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via a switch bank 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g. pacing rate, atrio-ventricular (AV) delay, atrial interconduction (A—A) delay, or ventricular interconduction (V—V) delay, etc.), as well as to keep track of the timing of refractory periods, PVARP intervals, noise detection windows, evoked response windows, alert intervals, marker channel timing, etc.

The switch bank 74 includes a plurality of switches for connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g. unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch bank 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch bank 74 determines the "sensing polarity" of the cardiac signal by selectively closing the appropriate switches. In this way, the clinician may program the sensing polarity independent of the stimulation polarity.

Each of the atrial sensing circuit 82 or the ventricular sensing circuit 84 preferably employs one or more low power, precision amplifiers with programmable gain and/or automatic gain control, bandpass filtering, and a threshold detection circuit, to selectively sense the cardiac signal of interest. The automatic gain control enables the stimulation device 10 to deal effectively with the difficult problem of sensing the low amplitude signal characteristics of atrial or ventricular fibrillation.

The outputs of the atrial and ventricular sensing circuits 82 and 84 are connected to the microcontroller 60 for triggering or inhibiting the atrial and ventricular pulse generators 70 and 72, respectively, in a demand fashion, in response to the absence or presence of cardiac activity, respectively, in the appropriate chambers of the heart. The atrial and ventricular sensing circuits 82 and 84, in turn, receive control signals over signal lines 86 and 88 from the microcontroller 60, for controlling the gain, threshold, polarization charge removal circuitry (not shown), and the timing of any blocking circuitry (not shown) coupled to the inputs of the atrial and ventricular sensing circuits 82 and 84.

For arrhythmia detection, the stimulation device 10 utilizes the atrial and ventricular sensing circuits 82 and 84 to sense cardiac signals, for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g. P-waves, R-waves, and depolarization signals associated with fibrillation which are sometimes referred to as "F-waves" or "Fib-waves") are then classified by the microcontroller 60 by comparing them to a predefined rate zone limit (e.g. bradycardia, normal, low rate VT, high rate VT, and fibrillation rate zones) and various other characteristics (e.g. sudden onset, stability, physiologic sensors, and morphology, etc.) in order to determine the type of remedial therapy that is needed (e.g. bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes.

Advantageously, the data acquisition system 90 may be coupled to the microcontroller 60 or another detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing circuitry within the microcontroller 60, and enabling the data acquisition system 90 via control signal 92 to sample the cardiac signal that falls in the capture detection window and, based on the amplitude of the sampled cardiac signal, determines if capture has occurred.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, stimulation pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. A feature of the stimulation device 10 is the ability to sense and store a relatively large amount of data (e.g. from the data acquisition system 90), which data may then be used for subsequent analysis to guide the programming of the stimulation device 10.

The operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through the established communication link 104.

In a preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g. detecting sleep and wake states). Accordingly, the microcontroller 60 responds by adjusting the various pacing parameters (such as rate, AV Delay, V—V Delay, etc.) at which the atrial and ventricular pulse generators 70 and 72 generate stimulation pulses.

While the physiologic sensor 108 is shown as being included within the stimulation device 10, it is to be understood that the physiologic sensor 108 may alternatively be external to the stimulation device 10, yet still be implanted within, or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors that sense the oxygen content of blood, pressure, cardiac output, ejection fraction, stroke volume, end diastolic volume, end systolic volume, respiration rate and/or minute ventilation, pH of blood, ventricular gradient, etc. However, any sensor may be used which is capable of sensing a physiological parameter that corresponds to the exercise state of the patient.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time, and also be capable of providing high-current pulses (for capacitor charging) when the patient requires a shock pulse. The battery 110 must preferably have a predictable discharge characteristic so that elective replacement time can be detected. Accordingly, the stimulation device 10 can employ lithium/silver vanadium oxide batteries.

The stimulation device 10 further includes a magnet detection circuitry (not shown), coupled to the microcontroller 60. The purpose of the magnet detection circuitry is to detect when a magnet is placed over the stimulation device 10, which magnet may be used by a clinician to perform various test functions of the stimulation device 10 and/or to signal the microcontroller 60 that an external programmer 102 is in place to receive or transmit data to the microcontroller 60 through the telemetry circuit 100.

As further shown in FIG. 2, the stimulation device 10 is shown as having an impedance measuring circuit 112 which is enabled by the microcontroller 60 by a control signal 114. Certain applications for an impedance measuring circuit 112 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of the valves, etc. The impedance measuring circuit 112 is advantageously coupled to the switch bank 74 so that any desired electrode may be used.

It is a function of the stimulation device 10 to operate as an implantable cardioverter/defibrillator (ICD) device. That is, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high (11 to 40 Joules) energy, as controlled by the microcontroller 60. Such shocking pulses are applied to the patient's heart through at least two shocking electrodes, and as shown in this embodiment, selected from the left atrial coil electrode 28, the RV coil electrode 36, and/or the SVC coil electrode 38 (FIG. 1). As noted above, the housing 40 may act as an active electrode in combination with the RV electrode 36, or as part of a split electrical vector using the SVC coil electrode 38 or the left atrial coil electrode 28 (i.e., using the RV electrode as common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 7:
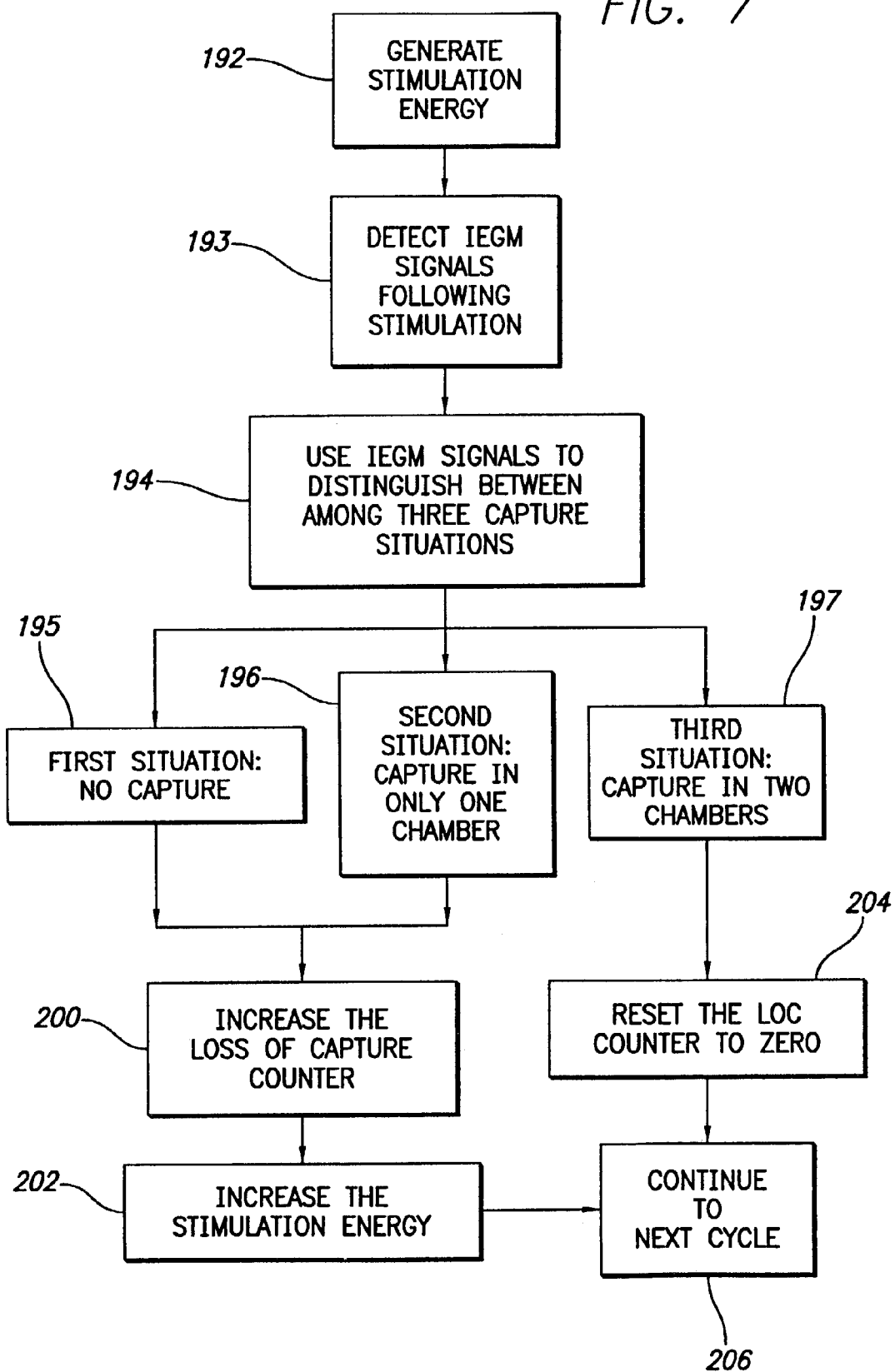
FIG. 7 is a flow chart depicting a high level method used by the stimulation device of FIGS. 1 and 2 for verifying capture during bi-ventricular (or bi-atrial) stimulation.

FIG. 7 illustrates a flow chart describing an overview of the operation and features implemented in one embodiment of the stimulation device 10. In this flow chart, and the other flow charts described herein, the various algorithmic steps are summarized in individual "blocks". Such blocks describe specific actions or decisions that must be made or carried out as the algorithm proceeds. Where the microcontroller 60 (or its equivalent) is employed, the flow charts presented herein provide the basis for a "control program" that may be executed or used by such a microcontroller 60 (or its equivalent) to effectuate the desired control of the stimulation device.

With reference to FIG. 2, and in accordance with the present invention, a morphology detector 64 is incorporated in the microcontroller 60 to allow for the processing of the sensed intra-cardiac electrogram signals (IEGM). IEGM sensing is achieved by receiving the atrial IEGM signals along the right atrial lead 20 through the atrial sensing circuit 82, or by receiving the ventricular IEGM signals along the right ventricular lead 30 or coronary sinus lead 24 through the ventricular sensing circuit 84.

In the embodiment described herein, the control program is comprised of multiple integrated program modules, with each module bearing responsibility for controlling one or more functions of the stimulation device 10. For example, one program module may control the delivery of stimulating pulses to the heart 12, while another may control the verification of ventricular capture and ventricular pacing energy determination. In effect, each program module is a control program dedicated to a specific function or set of functions of the stimulation device 10. In particular, a program module is implemented by the stimulation device 10 to perform capture verification during multi-chamber stimulation, more specifically during bi-ventricular stimulation.

In the stimulation device 10 or an equivalent system, bi-ventricular stimulation is achieved through the delivery of a ventricular stimulation pulse from the ventricular pulse generator 72 through the right ventricular lead 30 to stimulate the right ventricle, and the coronary sinus lead 24 to stimulate the left ventricle. Often, the output of the ventricular pulse generator 72 is connected to the right ventricular lead 30 and the coronary sinus lead 24 through a bifurcated connector.

The equivalent circuit 130 for bi-ventricular stimulation through a bifurcated connector is shown in FIG. 4A, where the total current, I, delivered to both ventricles is represented as the sum of the current, $I_R$, delivered to the right ventricle (RV), and the current, $I_L$, delivered to the left ventricle (LV). The current delivered to each ventricle will be equal the voltage, V, produced by the ventricular pulse generator 72, divided by the respective impedance of each ventricle as given by the following equations that correspond to the right ventricle and left ventricle, respectively:

$I_R = V/Z_R$, and $I_L = V/Z_L$, where $Z_R$ represents the total impedance through the right ventricle, and $Z_L$ represents the total impedance through the left ventricle.

For example, when the impedance $Z_L$ is greater than the impedance $Z_R$, then the current $I_L$ will be less than the current $I_R$. Thus, during bi-ventricular pacing, the right ventricle is typically captured at a lower stimulation pulse amplitude than the left ventricle. This leads to three capture situations during bi-ventricular stimulation: The first situation being no capture in either the right ventricle or the left ventricle due to sub-threshold stimulation; the second situation being capture in one ventricle only, typically the right ventricle; and the third situation being capture in both the left and the right ventricles. Therefore, it is desirable to distinguish these three capture situations based on the sensed IEGM. Since, according to one embodiment, the ventricular sensing circuit 84 is connected to both the right ventricular lead 30 and the coronary sinus lead 24 through the bifurcated connector, only one analog signal is received by the ventricular sensing circuit 84 providing input data from both the right ventricle and the right ventricle.

Figure 4B:
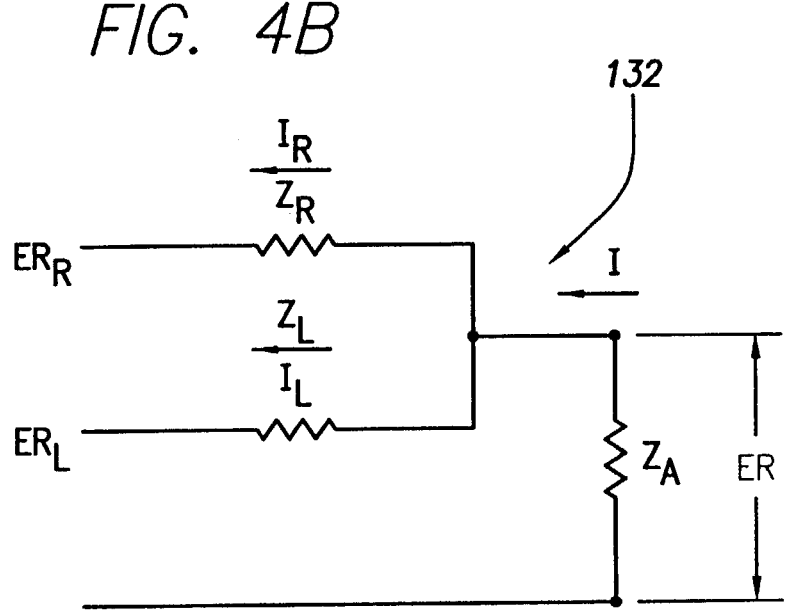
FIG. 4B is a circuit diagram representing an equivalent circuit of the stimulation device of FIG. 1 for bi-ventricular sensing.

The equivalent circuit 132 for the situation of bi-ventricular sensing is generally depicted in FIG. 4B. The evoked response, ER, measured by the ventricular sensing circuit 84, reflects the contribution of the evoked response $ER_R$ in the right ventricle, and the evoked response, $ER_L$, in the left ventricle. The parallel load of the sensing impedances $Z_R$ and $Z_L$ represents the connection to the right ventricle and the left ventricle, respectively, from the ventricular sensing circuit 84 that possesses an impedance $Z_A$. ZR represents the total sensing impedance through the right ventricle, and $Z_L$ represents the total sensing impedance through the left ventricle.

For example, when the impedance $Z_L$ is greater than the impedance $Z_R$, then the evoked response in the right ventricle, $ER_R$, presents a greater contribution than the evoked response in the left ventricle, $ER_L$, in the combined evoked response, ER, as measured by the ventricular sensing circuit.

In the situation where only one ventricle is captured, a conducted response in the other (or non-captured) ventricle will be delayed in time following the evoked response, ER, signal produced by the captured ventricle. Thus, two events will be detected by the ventricular sensing circuit 84.

Figure 5A:
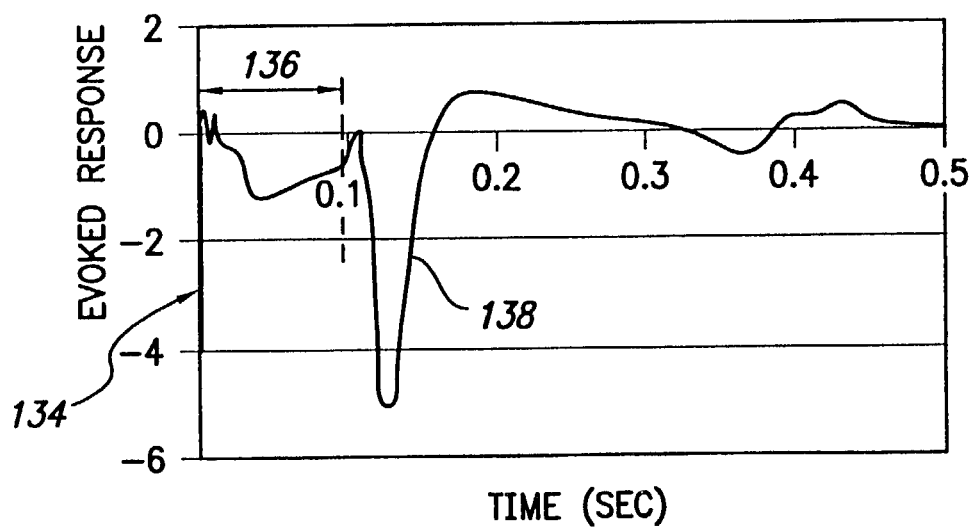
FIG. 5A represents an IEGM recording during sub-threshold bi-ventricular stimulation using the stimulation device of FIG. 1, and illustrates the failure to capture both the left and right ventricles.
Figure 5B:
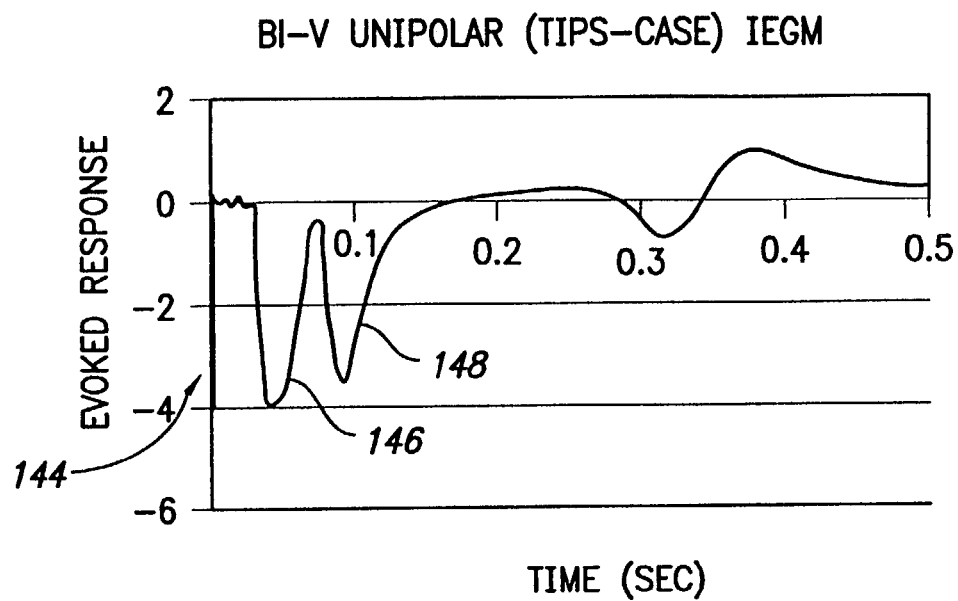
FIG. 5B represents an IEGM during bi-ventricular stimulation using the stimulation device of FIG. 1, in which only single-chamber capture is achieved.
Figure 5C:
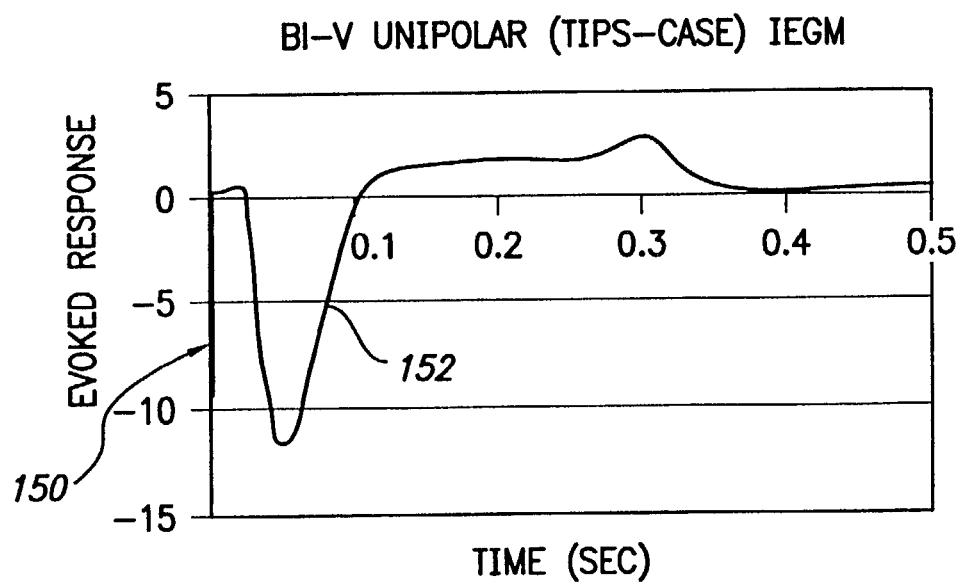
FIG. 5C illustrates an IEGM recording during bi-ventricular stimulation using the stimulation device of FIG. 1, in which successful capture of both ventricles is achieved.

As it will be appreciated from the description of FIGS. 5A through 5C, the morphology of the IEGM waveform is distinctly different during the above three capture situations. FIGS. 5A through 5C illustrate a method, according to one embodiment of the present invention, that enables the reliable detection of capture during bi-ventricular stimulation based on IEGM morphology.

FIG. 5A represents an IEGM recording during sub-threshold bi-ventricular stimulation, and illustrates the failure to capture both the left and right ventricles. A stimulation pulse 134 is followed by a time delay window 136, and a subsequent depolarization complex 138 (e.g. an intrinsic R-wave) that represents the intrinsic responses of the right and left ventricles. In this situation, the stimulation pulse amplitude is too low to depolarize either ventricle, and the natural depolarization is represented by the complex 138 associated with the depolarization of both ventricles.

FIG. 5B represents an IEGM during bi-ventricular stimulation in which only single-chamber capture is achieved. In this situation, the stimulation pulse 144 is followed immediately by an evoked response 146 that represents capture of one ventricle (i.e., the right ventricle), and a subsequent intrinsic depolarization complex 148 that corresponds to the conducted response in the ventricle that has not been captured (i.e., the left ventricle).

Figure 3A:
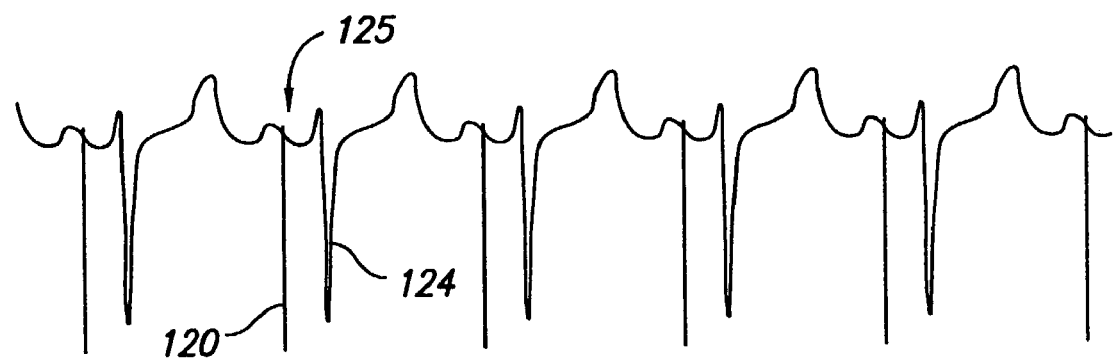
FIG. 3A represents a conventional surface ECG recording during sub-threshold bi-ventricular pacing, and illustrates the failure to capture both the left and right ventricles.
Figure 3B:
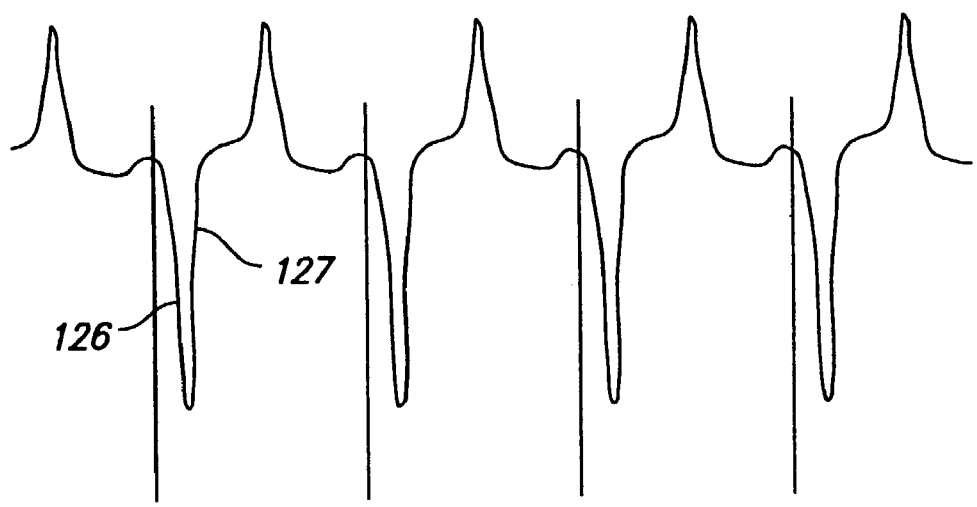
FIG. 3B represents a conventional surface ECG during bi-ventricular pacing in which only single-chamber capture is achieved.

This recording illustrates how the IEGM can be used to clearly discern between single-chamber and bi-ventricular capture. The stimulation pulse amplitude is sufficient to capture one ventricle (typically the right ventricle) as evidenced by the evoked response 146, but not sufficiently enough to capture the other ventricle (typically the left ventricle) as evidenced by the latent depolarization complex 148. The two responses 146 and 148 are distinct on the IEGM recording, and significantly simpler to discern compared to the two events that appear as a single complex 127 on the surface ECG recording of FIG. 3B.

FIG. 5C illustrates an IEGM recording during bi-ventricular stimulation in which successful capture of both ventricles is achieved. In this situation, a stimulation pulse 150 is immediately followed by an evoked response 152. No latent conducted response occurs, verifying that an evoked response occurred simultaneously in both ventricles with both responses represented by the evoked response 152.

Figure 6:
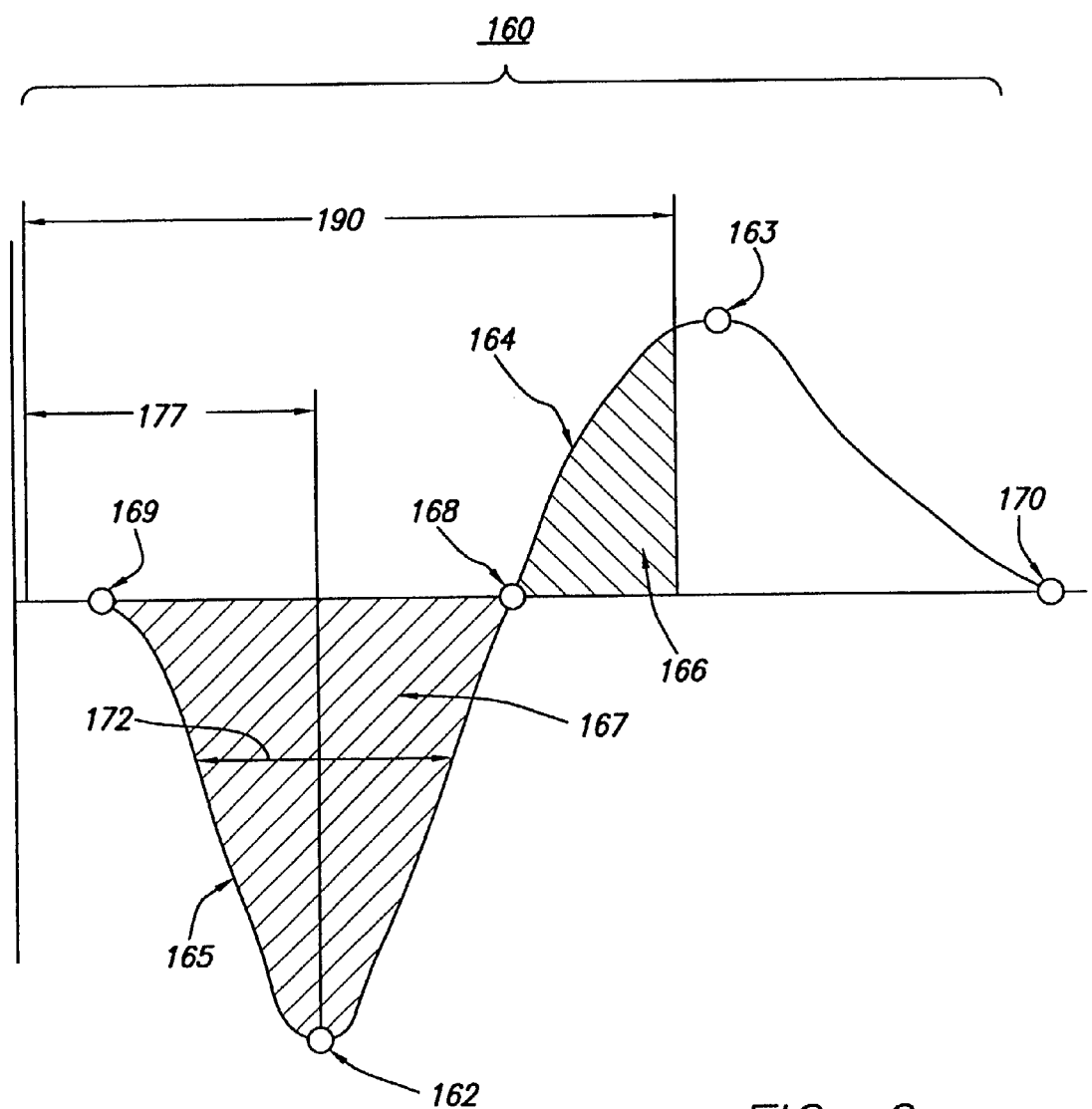
FIG. 6 is a graph illustrating IEGM waveform characteristics that can be determined by a morphology detector in accordance with one embodiment of the present invention.

In one embodiment of the present invention, the microprocessor 60 (FIG. 2) processes the IEGM waveforms and detects a number of parameters or characteristics defining the IEGM morphology. Exemplary characteristics are illustrated in FIG. 6 and include but are not limited to:
1) template representation of the overall IEGM waveform 160;
2) peak negative amplitude 162;
3) peak positive amplitude 163;
4) positive slope 164;
5) negative slope 165;
6) positive integral 166;
7) negative integral 167;
8) number of inflection points or zero crossings 168, 169, 170;
9) time duration (width) of depolarizations 172;
10) time interval 177 between the ventricular stimulation pulse and any subsequently detected events; and/or
11) time interval between detected events (not shown).

One or more of these IEGM characteristics are then used by the method of the present invention, as it will be described below, in order to distinguish between single-chamber capture, bi-ventricular capture, or complete loss of capture, based on comparisons made between an acquired IEGM during normal stimulation device operation and the known characteristics of the IEGM during the three capture situations.

In a preferred embodiment, IEGM characteristics representing the typical morphologies of the IEGM during (1) single-chamber capture, and (2) bi-ventricular capture, are stored in memory 94 (FIG. 2). These IEGM characteristics are acquired and stored during threshold testing performed at the time of device implant or at a follow-up office visit. During threshold testing, the ventricular stimulation pulse amplitude is progressively increased in small steps until single-chamber capture is recognized on the IEGM display. Once single-chamber capture is verified, the IEGM waveform is stored in memory as the single-chamber capture template.

Next, the ventricular stimulation pulse amplitude is further increased until bi-ventricular capture is recognized on the IEGM display. The IEGM waveform associated with bi-ventricular capture is then stored in memory as the bi-ventricular capture template. Other threshold-searching algorithms that are available to those practiced in the art, such as progressively decreasing the ventricular stimulation pulse amplitude, can also be used successfully in the implementation of the present invention for obtaining and storing single-chamber and bi-ventricular capture IEGM characteristics.

Thus, one important feature of the present invention is an automatic display feature which acquires and displays IEGM waveform morphologies. The automatic display may be annotated such that IEGM events, e.g. single-chamber evoked responses, bi-ventricular evoked responses, conducted responses, and bi-ventricular intrinsic responses are clearly indicated. Such annotation allows a medical practitioner to easily distinguish between the various capture situations.

FIG. 7 is a flow-chart that illustrates a high level method for automatically verifying stimulation capture in one or more cardiac chambers according to one embodiment of the present invention. The method starts at step 192 by generating stimulation pulses.

At step 193, the method detects intracardiac electrogram (IEGM) signals in the one or more chambers subsequent to the delivery of the stimulation pulses. Using the IEGM signals detected at step 193, the method 191 distinguishes among three capture situations in the cardiac chambers, at step 194. These three capture situations include: a first situation that depicts the absence of capture in both chambers due, for example, to sub-threshold stimulation; a second situation that depicts capture in only one of the cardiac chambers; and a third situation that depicts capture in two chambers.

In the event that there is non-capture or single-chamber capture (steps 195 or 196, respectively), then the loss of capture counter is incremented (step 200), and the stimulation energy is increased in step 202. The method then returns to step 206 and continues with the pacing routine for the next pacing cycle.

In the event that there is capture in both chambers (step 197), then the loss of capture counter is reset to zero. The method then also returns to step 206 and continues with the pacing routine for the next pacing cycle. The purpose of the loss of capture counter is to detect "n" loss of capture beats such that a threshold search can be triggered.

Figure 8:
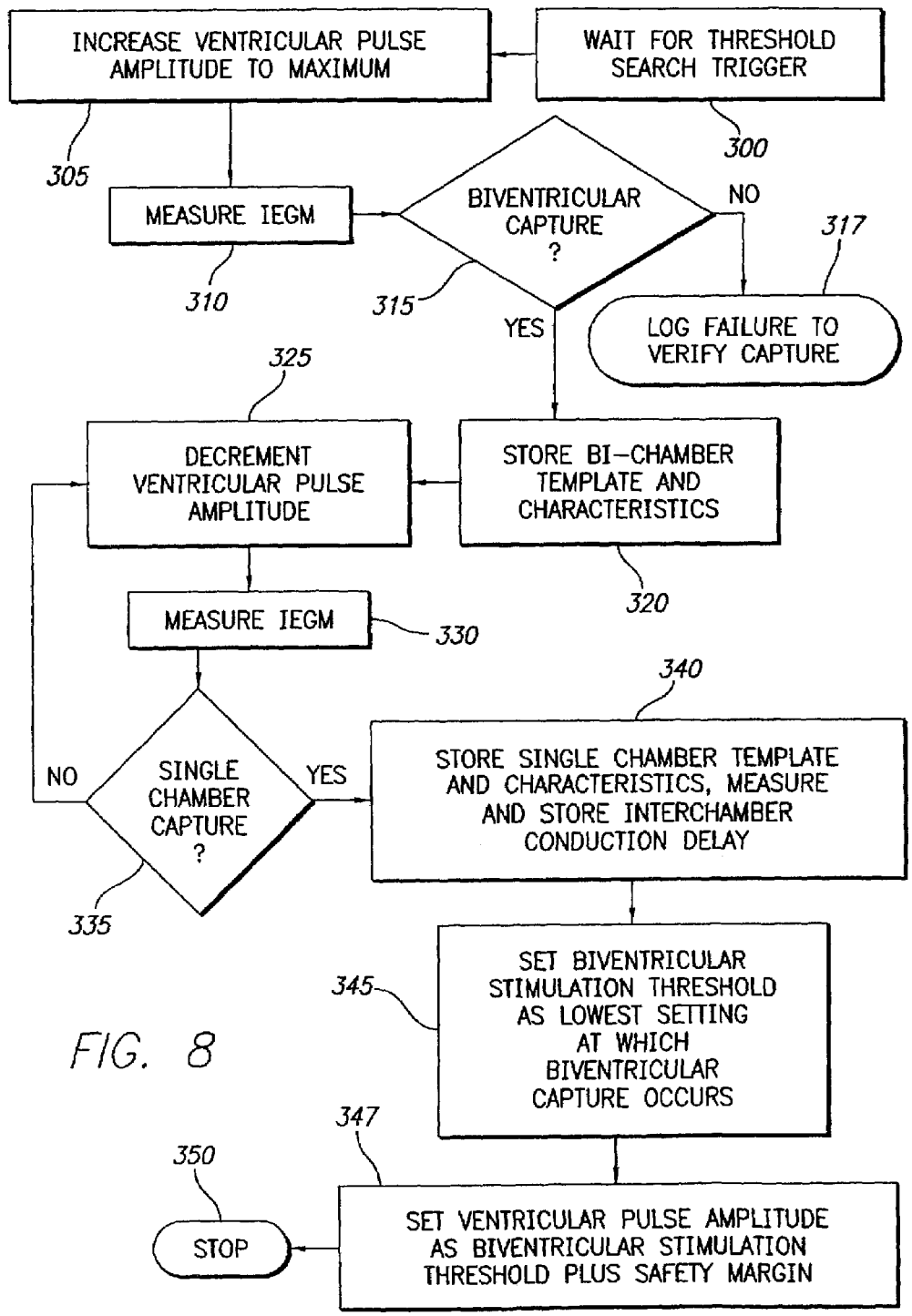
FIG. 8 is a flow chart depicting a method used by the stimulation device of FIGS. 1 and 2 for determining the capture state, the corresponding IEGM waveform characteristics during bi-ventricular (or bi-atrial) stimulation.

With reference to FIG. 8, a threshold search method could be initiated at step 305 by the microcontroller 60 when loss of bi-ventricular capture is suspected (e.g., after "n" loss of capture events) or after every "m" hours as programmed or as needed at implant or at follow-up. The method is initiated at step 305 by increasing the ventricular stimulation pulse amplitude, $P_V$, to a maximal value, $P_{VMAX}$. The IEGM waveform is then sampled and stored at step 310. The IEGM waveform is processed by the morphology detector 64 such that microprocessor 60 can verify that bi-ventricular capture has indeed occurred.

Step 315 represents an algorithm in which IEGM properties as determined by the morphology detector 64 are compared to specific criteria that would indicate bi-ventricular capture. A plurality of parameters may be used for determining if a single depolarization complex, representing the evoked response of both ventricles, has occurred immediately following the stimulation pulse. For example, with reference to FIG. 6, the number of negative peaks 162 detected within a sampling window 190 would indicate if one or more depolarizations have occurred following the stimulation pulse. Timing intervals may also be compared. For example, if a negative peak 162 is detected within a short period of time, for example 16 to 40 msec, the depolarization is interpreted as an evoked response. If the depolarization occurs later in time but still within the sampling window 190, the depolarization is interpreted as an intrinsic response indicating failure to capture either ventricle, even at the temporary high stimulation energy. This situation would imply a system failure that would be flagged in memory at the termination step 317.

Once bi-ventricular capture is verified at step 315, the IEGM waveform is stored as the new bi-ventricular template at step 320 and further processed by the morphology detector 64 such that the bi-ventricular waveform characteristics can be stored in memory 94 (FIG. 2).

Next, the ventricular stimulation pulse amplitude, Pv, is decreased at step 325 by a pre-defined value, p. Another IEGM waveform is sampled and stored at step 330. At decision step 335, the new IEGM waveform is examined in a similar manner as in step 315 but this time the algorithm tests for criteria indicating single-chamber capture, that is two distinct depolarizations occurring after the stimulation pulse (FIG. 5B). For example, two depolarizations may be detected by two negative peaks (FIG. 6) following the stimulation pulse within the sampling window 190, a second event detection at some time interval after a first event detection, a large value of the negative integral, or any of a number of other methods associated with the characteristics determined by the morphology detector 64 and illustrated, for example, in FIG. 6.

If the criteria required to verify single-chamber capture are not met, the ventricular stimulation pulse amplitude, $P_V$, is decreased again at step 325, and the foregoing process is repeated until single-chamber capture is verified. Once detection of single-chamber capture is verified, the IEGM waveform is stored in memory as the new single-chamber capture template at step 340 and further processed by the morphology detector 64 such that the single-chamber capture waveform characteristics can be stored in memory 94 (FIG. 2). Furthermore, the time delay between two negative peaks, the inter-chamber conduction delay, can be measured and stored at step 340.

The lowest setting at which bi-ventricular capture continues to occur, that is the pulse energy prior to the last decrement of the ventricular stimulation pulse amplitude, $P_V$, is stored in the memory 94 at step 345 as the bi-ventricular stimulation threshold, T. At step 347, the ventricular pulse amplitude $P_V$ is set equal to T, or T plus some programmed safety margin (SM), and the method 300 is terminated at block 350. In this way, bi-ventricular capture is regained with the newly acquired capture verification IEGM characteristics stored in memory 94, and the stimulation device 10 can return to normal operation with ongoing monitoring of bi-ventricular capture.

A further aspect of the present invention is the ability to monitor the progression of CHF. This is achieved through the determination of temporal characteristics of the IEGM waveform, particularly during single-chamber capture by the morphology detector 64. As the severity of CHF worsens, inter-ventricular conduction time increases due to further dilation of the ventricles. IEGM acquisition and storage therefore provides a method for monitoring inter-ventricular conduction time as a means for monitoring the progression of CHF. If, during single-chamber capture, the time elapsed between a negative peak detection 146 (FIG. 5B) to the next negative peak detection 148 increases, which indicates that interventricular conduction delay has worsened such that hemodynamic performance has been deteriorating.

An added feature of the present invention, as aforementioned in Step 340 in FIG. 8, is a means to monitor CHF progression by monitoring inter-ventricular conduction time during bi-ventricular threshold testing and IEGM template acquisition. Inter-ventricular conduction time, measured as the time between two negative deflecting depolarizations 146, 148, is stored in memory 94 (FIG. 2), and is made available to the physician during patient follow-up visits. Inter-ventricular conduction time could also be used as a closed-loop feedback parameter within the stimulation device 10 to cause automatic adjustments of pacing parameters such that pacing therapy is optimized as CHF worsens or improves.

Thus, an implantable cardiac device and method for reliably detecting and verifying capture during bi-ventricular pacing as well as a means for monitoring progression of CHF by monitoring inter-ventricular conduction time are provided.

While the invention has been described with reference to particular embodiments, modifications could be made thereto by those skilled in the art without departing from the spirit and scope of the present invention.

What is claimed is:

1. A system for verifying capture in the ventricles of a patient's heart, the system comprising:
means for stimulating the ventricles;
means for sensing an evoked response signal resulting from stimulating the ventricles; and means for processing the evoked response signal to distinguish between capture of both chambers and a loss of capture in at least one chamber.

2. The system according to claim 1, wherein the means for stimulating the ventricles comprises:
means for generating stimulation pulses in each of the corresponding chambers of the patient's heart.

3. The system according to claim 1, wherein the means for stimulating comprises means for increasing an energy level component of a stimulation pulse in response to a detection of loss of capture.

4. The system according to claim 1, wherein the means for processing the evoked response signal comprises means for distinguishing between capture of both chambers, loss of capture in one chamber, and loss of capture in both chambers.

5. The system according to claim 1, wherein the means for sensing comprises means for sensing at least one characteristic of the evoked response signals occurring in both chambers, the characteristic providing an indication of capture or non-capture of two corresponding chambers of the patient's heart.

6. The system according to claim 5, wherein the means for sensing comprises means for sensing at least one of the following characteristics in the composite bi-chamber cardiac signal:
a template representation of an overall intra-cardiac electrogram (IEGM) waveform;
a peak negative amplitude;
a peak positive amplitude;
a positive slope;
a negative slope;
a positive integral;
a negative integral;
a plurality of inflection points;
an average time duration of a plurality of depolarizations;
a time interval between a stimulation pulse and any subsequently detected event; and
a time interval between consecutively detected events.

7. A method for verifying capture during bi-ventricular stimulation of a patient's ventricles, the method comprising:
delivering stimulation pulses to the ventricles;
detecting evoked response signals subsequent to the delivery of the stimulation pulses; and
processing the evoked response signals to detect a plurality of capture situations of the two corresponding chambers.

8. The method according to claim 7, wherein determining a plurality of capture situations comprises distinguishing among the following capture situations: loss of capture in both ventricles, capture in only one of the ventricles, and capture in both ventricles.

9. The method according to claim 8, and further comprising increasing a stimulation pulse energy of the stimulation pulses when there is loss of capture in at least one of the ventricles.

10. The method according to claim 7, wherein processing the evoked response signals comprises classifying the evoked response signals based on at least one of the following parameters:
a template representation of an overall intra-cardiac electrogram (IEGM) waveform;
a peak amplitude;
a positive slope;
a negative slope;
a positive integral;
a negative integral;
a plurality of inflection points;
an average time duration of a plurality of depolarizations;
a time interval between a stimulation pulse and any subsequently detected event; and
a time interval between consecutively detected events.

11. The method according to claim 7, further comprising storing IEGM capture characteristics representative of typical IEGM morphologies during non-capture of both chambers, single-chamber capture, and bi-chamber capture, and wherein processing the evoked response signals comprises comparing the evoked response signals with the IEGM capture characteristics.

12. A system for verifying capture in the ventricles of a patient's heart, the system comprising:
a pulse generator that is operative to generate stimulation pulses to be delivered to the ventricles;
a lead system connected to the pulse generator and configured for placement in electrical communication with the ventricles;
a sensor that is operative to sense an evoked response signal resulting from the stimulation pulses being delivered to the ventricles; and
a processor connected to the sensor and operative to process the evoked response signal to distinguish between capture of both chambers and a loss of capture in at least one chamber.

13. The system according to claim 12, wherein the lead system comprises a pair of leads configured for placement in, respectively, a right ventricle and in a coronary sinus region.

14. The system according to claim 12, further comprising a controller connected to the processor and pulse generator, wherein the controller is operative to control the pulse generator to increase an energy level component of a stimulation pulse in response to a detection of loss of capture by the processor.

15. The system according to claim 12, wherein the processor is operative to distinguish between capture of both chambers, loss of capture in one chamber, and loss of capture in both chambers.

16. The system according to claim 12, wherein the processor is operative to detect at least one of the following characteristics in the evoked response signals:
a template representation of an overall intra-cardiac electrogram (IEGM) waveform;
a peak negative amplitude;
a peak positive amplitude;
a positive slope;
a negative slope;
a positive integral;
a negative integral;
a plurality of inflection points;
an average time duration of a plurality of depolarizations;
a time interval between a stimulation pulse and any subsequently detected event; and
a time interval between consecutively detected events.

* * * * *